United States Patent
Tu et al.

[11] Patent Number: 5,376,110
[45] Date of Patent: Dec. 27, 1994

[54] METHOD OF MANUFACTURING PLIABLE BIOLOGICAL GRAFTS MATERIALS

[75] Inventors: Roger Tu, Tustin; Edwin Wang; Chris Kuo, both of Irvine; Cary Hata, Alhambra, all of Calif.

[73] Assignee: Baxter International Inc., Deerfield, Ill.

[21] Appl. No.: 74,018

[22] Filed: Jun. 9, 1993

Related U.S. Application Data

[63] Continuation of Ser. No. 656,656, Feb. 14, 1991, abandoned.

[51] Int. Cl.5 .................... A61F 2/06; A61F 2/04
[52] U.S. Cl. ............................ 623/1; 623/12; 600/36; 128/DIG. 8
[58] Field of Search ........... 623/1, 11, 12, 13; 128/DIG. 8; 600/36

[56] References Cited

U.S. PATENT DOCUMENTS

| | | | |
|---|---|---|---|
| 2,900,644 | 8/1959 | Rosenberg et al. | 3/1 |
| 3,937,422 | 12/1975 | Sawyer | 3/1 |
| 3,966,401 | 6/1976 | Hancock et al. | 8/94 |
| 3,974,526 | 8/1976 | Dardik et al. | 3/1 |
| 3,988,782 | 11/1976 | Dardik et al. | |
| 4,098,571 | 7/1978 | Miyata et al. | 8/94 |
| 4,252,759 | 2/1981 | Yannas et al. | 264/86 |
| 4,544,599 | 10/1985 | Buttazoni | 428/262 |
| 4,553,974 | 11/1985 | Dewanjee | 8/94 |
| 4,725,671 | 2/1988 | Chu et al. | 530/356 |
| 4,776,853 | 10/1988 | Klement et al. | 8/94 |
| 4,801,299 | 1/1989 | Brendel et al. | 623/1 |
| 4,806,595 | 2/1989 | Noishiki et al. | 623/1 |
| 4,990,131 | 2/1991 | Dardik et al. | 600/36 |

FOREIGN PATENT DOCUMENTS

| | | |
|---|---|---|
| 086150 | 8/1983 | European Pat. Off. |
| 128043 | 12/1984 | European Pat. Off. |
| 179600 | 4/1985 | European Pat. Off. |
| 320441 | 6/1989 | Germany |
| 8200091 | 1/1982 | WIPO ................... 623/1 |
| WO83/03536 | 10/1983 | WIPO |

Primary Examiner—David Isabella
Assistant Examiner—Debra S. Brittingham
Attorney, Agent, or Firm—Stetina & Brunda

[57] ABSTRACT

Preparing chemically cross-linked collagenous biological graft material by preparation processes which include the step of altering the locations and/or orientations of chemical cross-linkages formed during the collagen cross-linking process. Embodiments of the method include various processes whereby physical force, stress or movement is applied to alter the relative positioning of the collagen fibers within the graft materials during at least the initial period of exposure to the collagen cross-linking reagent.

8 Claims, 4 Drawing Sheets

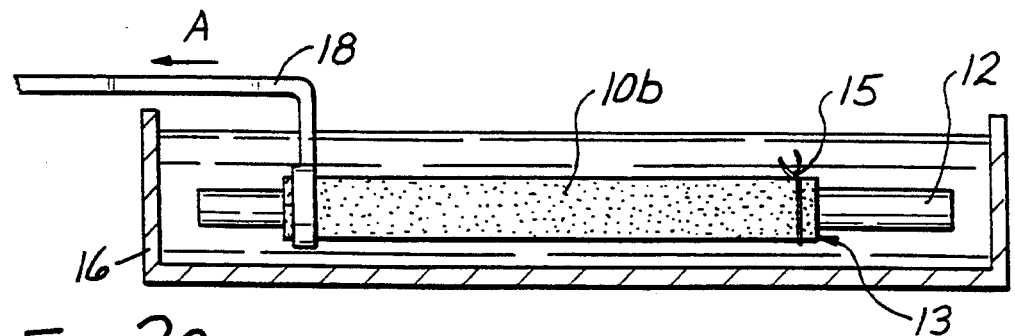
Fig. 2c
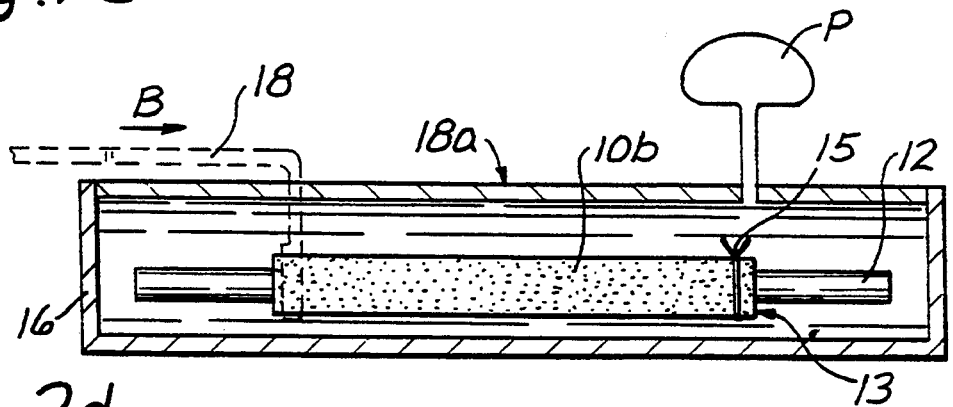
Fig. 2d
Fig. 2e
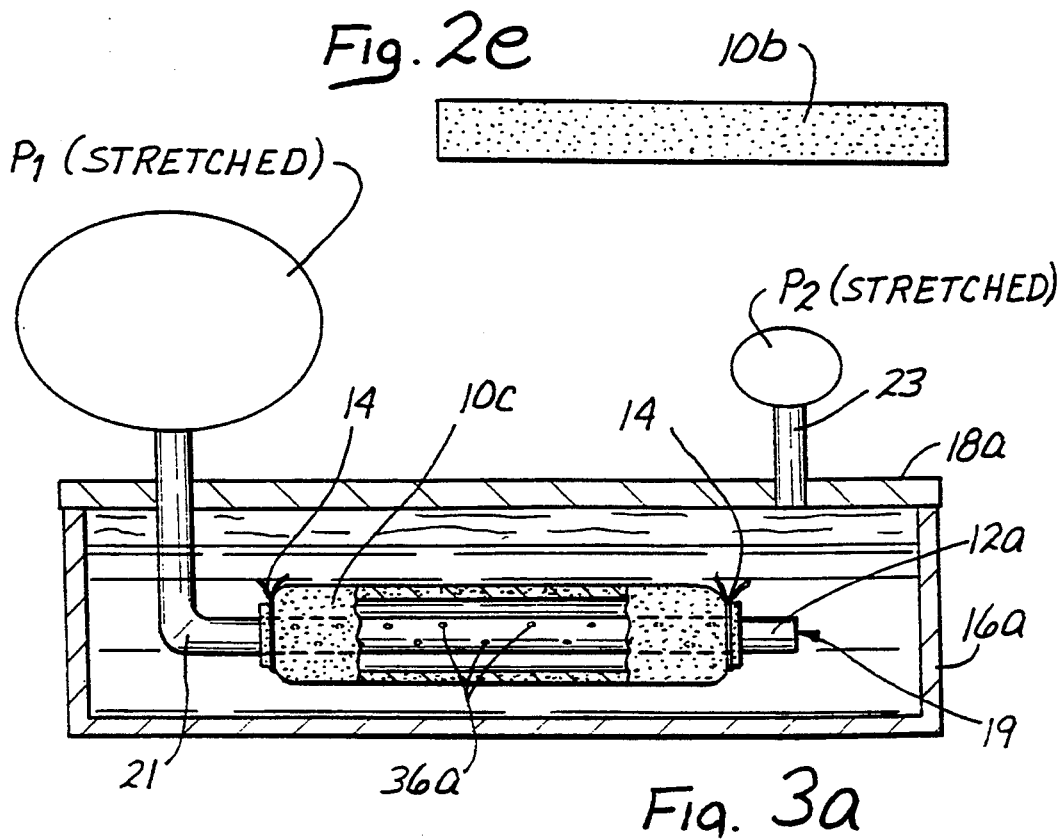
Fig. 3a

METHOD OF MANUFACTURING PLIABLE BIOLOGICAL GRAFTS MATERIALS

RELATED CASES

This application is a continuation of co-pending U.S. application Ser. No. 07/656,656, filed on Feb. 14, 1991, now abandoned.

FIELD OF THE INVENTION

This invention relates generally to the preparation of biological tissue grafts and more improved methods of preparing chemically cross-linked collagenous graft materials having improved flexibility and pliability.

BACKGROUND OF THE INVENTION

Natural tissues obtained from mammalian sources have been used for allogenic and xenogeneic grafting for many years. For example, certain cardiovascular tissues (e.g. segments of blood vessel, heart valves) have been harvested from human or other mammalian sources and subsequently surgically implanted in the human body.

Many of the biological tissues which one desires to harvest and prepare for subsequent surgical implantation contain substantial amounts of connective tissue. The function of the connective tissue is to provide a supportive frame work within which other functional cell types (e.g. muscle fibers) are disposed. Connective tissues are largely formed of insoluble proteins collagen and elastin. Collagen and elastin exist in the form of insoluble fibers. Such insoluble fibrils are arranged within a continuous matrix called the ground substance. The flexibility and other characteristics of the connective tissue depend largely on the proportions of collagen and elastin contained within such tissue, and the structure and configuration of the collagen/elastic fiber network thereof.

As illustrated in FIGS. 5a–5c herein, each collagen molecule consists of three polypeptide chains intertwined in a coiled helical conformation. The individual amino acid constituents of each polypeptide chain are connected, by hydrogen bonds, to individual amino acids of an adjacent polypeptide chain, thereby holding the individual polypeptide chains in the triple helical conformation shown in FIG. 5c.

The current methods of preserving and preparing collagenous, biological tissues for subsequent surgical implantation include the step of "fixing" the collagen network by exposing the tissue to one or more chemical compounds capable of cross-linking the collagen molecules within the tissue. Both intermolecular (FIG. 5b) and intramolecular (FIG. 5c) cross-linkages may be formed by the currently known fixative compounds.

Chemical compounds which are known to cross-link collagen include formaldehyde, glutaraldehyde, dialdehyde starch, hexamethylene diisocyanate and certain polyepoxy compounds including glycol diglycidyl ether, polyol polyglycidyl ether and dicarboxylic acid diglycidylester. Three (3) specific water soluble polyepoxy compounds which may be used as collagen cross-linking agents are shown below:

1. Difunctional epoxy Ethylene glycol diglycidyl ether (molecular weight=270)

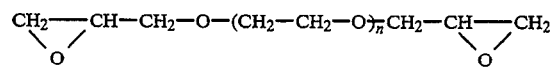

(wherein: n=1)

(Denacol ™ Ex-810; Nagase Chemicals, Ltd., Osaka, Japan)

2. Trifunctional epoxy Glycerol Triglycidyl ether (molecular weight=435)

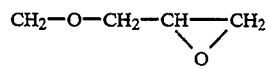

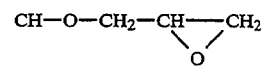

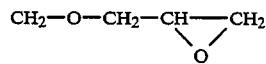

(Denacol ™ Ex-313; Nagase Chemicals, Ltd., Osaka, Japan

3. Tetrafunctional epoxy Sorbitol tetraglycidyl ether (molecular weight=680)

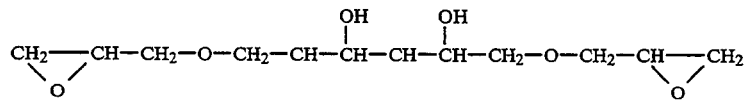

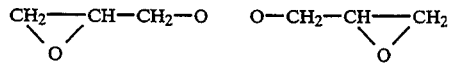

(Denacol ™ Ex-612; Nagase Chemicals, Ltd., Osaka, Japan)

In general, the low molecular weight chemical fixatives, such as glutaraldehyde, are relatively fast acting. On the other hand, high molecular weight fixatives, such as polyepoxy compounds, are relatively slow acting. Thus, the exposure time required to effect adequate cross-linking of a collagenous graft depends on the molecular weight and functionality (i.e. the reactivity) of the cross-linking reagent being used.

Examples of biological graft materials and methods of preparation thereof are described in U. S. Pat. Nos. 2,900,644 (Rosenberg et al.), 3,927,422 (Sawyer), 3,966,401 (Hancock et al.), 3,974,526 (Dardik et al.), 4,239,492 (Holman et al.), 4,466,139 (Ketharanathan et al.) and 4,806,595 (Noishiki et al.).

One drawback associated with the use of chemically cross-linked collagenous graft materials is that the cross-linking of the collagen molecules within the graft typically results in undesirable stiffness and a loss of pliability. Such stiffening or loss of pliability may render the biological graft difficult to suture and difficult to manipulate during surgical implantation. In particular, with respect to arterial vascular grafts, the unnatural stiffness of an implanted biological graft may result in poor hemodynamic performance of the graft, with possible resultant clinical failure thereof. See, Abbott W. M. and Cambria, R. P., Control of Physical Characteristics-Elasticity and Compliance of Vascular Grafts; BIOLOGIC AND SYNTHETIC VASCULAR PROSTHESES, Stanley, J. C. et al. (ed) (Grune & Stratton, 1982).

In view of the undesirable stiffness of chemically cross-linked collagenous biological graft materials of the prior art, there exists a need for the development of improved methods of preparing and preserving such collagenous biomaterials whereby the resultant stiffness and lack of pliability may be avoided or minimized.

The graft preparation methods of the present invention are particularly applicable to, though not limited to, the preparation of vascular grafts such as coronary artery bypass grafts. Indeed, blood vessels are known to contain relatively large amounts of collagen. The quantity of collagen found in a particular blood vessel appears to vary with the types of mechanical forces which affect that blood vessel under normal physiological conditions. In vessels which typically encounter low pressure (e.g. small veins) the collagen content relative to the diameter of the vessel is low. On the other hand, in vessels which encounter high pressure (e.g. arteries) the collagen content relative to the diameter of the vessel is high. Indeed, collagen is known to constitute approximately 20% of the dry weight of some large elastic arteries and perhaps up to 50% of the dry weight of some smaller peripheral arteries.

Thus, in view of: (a) the desirability of using preserved collagenous biological tissues (e.g. blood vessels) for allogenic or xenogeneic grafting and (b) the propensity for such collagenous tissues to become stiff when treated with the known collagen cross-linking reagents, it is desirable to develop new methods of preserving or fixing such collagenous graft materials so as to improve the resultant pliability and flexibility thereof.

SUMMARY OF THE INVENTION

The present invention overcomes some or all of the foregoing shortcomings of the prior art by providing an improved method for preparing collagenous biomaterial for subsequent surgical implantation into the human body. In general, the invention comprises a method of preparing chemically cross-linked collagenous biological materials wherein the locations and/or orientations of the chemical cross-linkages formed within and/or between collagen molecules are caused to be altered from those which would normally be formed if the graft material were to be immersed in or otherwise exposed to chemical collagen cross-linking chemicals while in an unstressed relaxed state.

One means by which the locations and/or orientations of the collagen cross-linkages may be altered, in accordance with the present invention, is by physically changing the relative spacial and positional relationships of the individual collagen fibers and/or molecules within the tissue during at least a portion of the chemical cross-linking (i.e. chemical fixation) process. Such changes of spacial or positional relationships of the collagen fibers may be accomplished by physically stressing, moving, relocating, vibrating or otherwise applying force to the graft material. Such changing of the relative spacial or positional relationships of the collagen fibers and/or collagen molecules will result in modification of the locations and/or orientation of the chemical cross-linkage formed between and/or within collagen molecules as opposed to the locations and orientations of chemical cross-linkages which would normally have been formed if the chemical cross-linking process had been carried out without such physical movement, stressing or physical relocation of the individual collagen fibers.

In accordance with the invention, the physical movement, stressing or relocation of the collage fibers may be carried out by exerting physical force on the graft material while the graft material is immersed in a collagen cross-linking reagent. The exertion of force upon the graft material that may be carried out statically while the graft material remains exposed to the cross-linking reagent or may constitute a dynamic process whereby the exertion of force upon and/or movement of the graft material is carried out intermittently and repeatedly during at least a portion of the time that the graft material remains exposed to the collagen cross-linking reagent.

Further in accordance with the invention, the network of collagen fibers within the graft material may be compressed while the collagen fibers are exposed to a collagen cross-linking reagent. In cases where the graft material is of elongate tubular configuration (e.g. a blood vessel), the elongate graft may be physically compressed along its longitudinal axis and subsequently held in such longitudinally compressed state while being immersed in a collagen cross-linking reagent.

Further in accordance with the invention, the network of collagen fibers within the graft material may be alternately (a) stretched and (b) relaxed during at least a part of the time that the collagen fibers are exposed to a collagen cross-linking reagent. In cases where the graft material is of elongate tubular configuration (e.g. a blood vessel), the alternate stretching and relaxing may constitute longitudinal stretching/relaxing along the longitudinal axis of the graft or radial stretching/relaxing whereby the circumference of the tubular graft is alternately enlarged and relaxed.

In accordance with a still further aspect of the invention, the network of collagen fibers within the graft material may be alternately compressed and relaxed while the collagen fibers are exposed to a collagen cross-linking reagent. In cases where the biological graft material is of an elongate tubular configuration (e.g. a blood vessel), the intermittent compression/relaxation may comprise longitudinal compression/relaxation along the longitudinal axis of the graft or radial stretching/relaxing whereby the circumference of the tubular graft is alternately enlarged and relaxed.

The methods of preparing collagenous biological graft materials of the present invention may be utilized in conjunction with any type of collagen cross-linking reagent. However, the time of application of the methods of the present invention may vary, depending on the reactivity of the particular cross-linking reagent being used.

Various additional aspects, objects and advantages of the present invention will become apparent to those skilled in the art upon reading and understanding of the following detailed description and the accompanying drawings.

BRIEF DESCRIPTION OF THE DRAWINGS

FIGS. 2a–2e is a schematic diagram of a preferred method of preparing vascular grafts dynamic longitudinal stretching;

FIGS. 3a–3b is a diagram of a method and apparatus for preparing pliable vascular grafts by dynamic radial stretching;

DETAILED DESCRIPTION OF THE PREFERRED EMBODIMENT

The following detailed descriptions and the examples set forth therein are provided for the purpose of describing and illustrating presently preferred embodiments of the invention. The following detailed description and examples of the presently preferred embodiments are not intended to limit the scope of the claims in any way.

A. First Embodiment: Static Retraction or Compression of the Collagenous Network during Fixation One embodiment of this invention comprises placing and holding the collagenous graft material in a compressed (i.e. retracted) state during exposure to one or more collagen cross-linking agents.

In accordance with this embodiment of the invention, as illustrated in FIGS. 1a–1d, the collagenous graft material (e.g. a segment of blood vessel) may be disposed on the surface of a tube, rod, mandrel, plate, jig or other form member. Preferably, the surface of the form member is smooth and compatible with the configuration of the graft. The graft is then caused to remain in such compressed or retracted state by attachment of a holding apparatus 14 such as clips, clamps, sutures or tie wraps. The graft is caused to remain in such compressed or retracted state during at least the initial phase of the collagen cross-linking reaction as may be accomplished by immersing the retracted graft material in a pool of collagen cross-linking fixative solution.

The amount of compression or retraction applied will vary, depending on the type of collagenous tissue being treated. In vascular applications, it is preferable that an elongate segment of blood vessel be longitudinally shortened by an amount equal to about 1% to 50% of its original relaxed length and most preferably 5% to 30% of its original relaxed length.

EXAMPLE 1

Preparation of a Pliable Coronary Artery Bypass Graft Under Static Longitudinal Retraction or Compression A segment of bovine coronary artery 10a is removed from a donor animal and cut to a desired length (hereinafter referred to as the "relaxed length"). After the harvested segment of artery 10a has been thoroughly cleaned with sterile saline solution, any excess surrounding connective tissue is trimmed away using standard surgical instruments. Additionally, any unwanted branches of the artery are ligated through the use of standard surgical technique and surgical suture materials.

After such cleaning, trimming and ligation procedures have been completed, the segment of artery 10a is slidably advanced onto the outer surface of a cylindrical rod or other cylindrical support member 12. The cylindrical support member 12 preferably has a diameter which is equal to or slightly larger than the internal diameter of the artery.

Figure 1A:
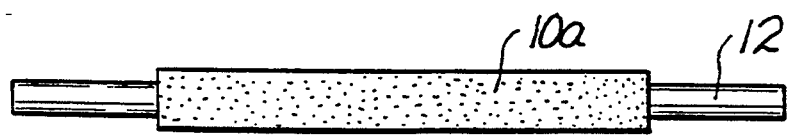
FIGS. 1a–1d is a schematic diagram illustrating a preferred method of preparing vascular grafts by static longitudinal retraction.
Figure 1B:
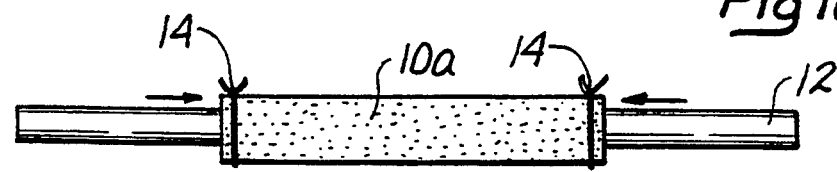
Figure 1C:
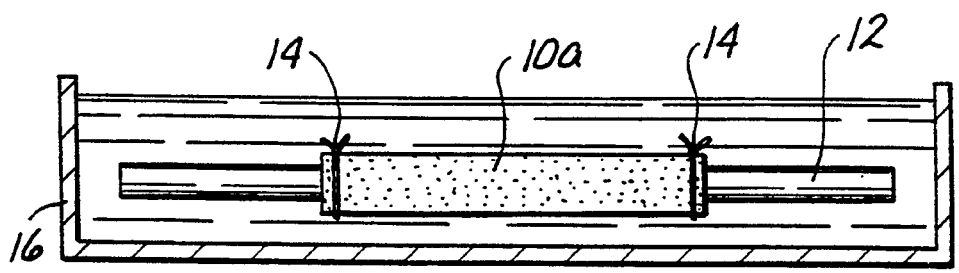
Figure 1D:
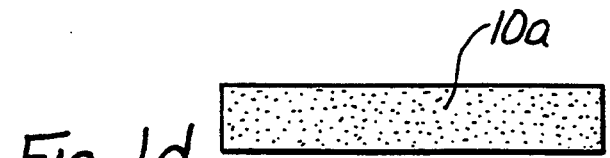

After the artery 10a has been disposed upon cylindrical support member 12, the segment of artery 10a is longitudinally compressed or retracted to a desired "compressed length" and ligatures or clips 14 are placed around the ends of the segment of artery 10a to hold the segment of artery 10a in the longitudinally retracted or compressed state. (FIG. 1b). While being maintained in such retracted or compressed state, the segment of artery 10a is immersed (FIG. 1c) in a bath 16 of chemical fixative solution (FIG. 1c). In this example the fixative solution comprises 2% by volume aqueous solution of glycerol triglycidyl ether (MW 435) Denacol ™ Ex-313; Nagase Chemicals Ltd., Osaka, Japan). This fixative solution is maintained at room temperature and buffered to a Ph of approximately 10.0 by addition of 0.1N carbonate-bicarbonate buffer solution. Other Denacol ™ epoxy materials may also be used as described in U.S. Pat. No. 4,806,515. The entire disclosure of U.S. Pat. No. 4,806,515 is expressly incorporated herein by reference for the purpose of disclosing the chemical compositions, properties and methods of application of the specific Denacol ™ epoxy materials as fixatives in this invention.

It is preferable that the segment of artery 10a remain in the 2% Denacol ™ Ex-313 solution at room temperature and ambient pressure for about 10–80 hours, and most preferably about 20–60 hours. In this particular example the segment of artery 10a remained immersed in the 2% Denacol ™ Ex-313 fixative solution at room temperature and ambient pressure for a total of 66 consecutive hours.

After 66 hours of immersion in the fixative bath 16, the segment of artery 10a was removed from the bath 16, ligatures 14 were removed and the segment of artery 10a was slidably extracted from the outer surface of the cylindrical support member 12.

TABLE 1, below, contains modulus of elasticity data for one (1) fresh untreated segment of bovine coronary artery (control) and six (6) segments of bovine carotid artery treated in accordance with this example. As shown, the six (6) segments of artery were compressed or retracted to lengths which were 0%, 10%, 20%, 30%, 40% and 50% than the respective original unretracted length, of each segment of artery.

TABLE 1

| Sample No. | Relaxed Length (cm) | Compressed Length (cm) | % Retraction | Modulus of Elasticity (psi) |
|---|---|---|---|---|
| A | 9.1 | 9.1 | 0 | 59.2 |
| B | 10.5 | 9.4 | 10 | 45.4 |
| C | 9.0 | 7.2 | 20 | 25.9 |
| D | 10.7 | 7.9 | 30 | 23.5 |
| E | 11.5 | 6.9 | 40 | 22.9 |
| F | 10.2 | 5.1 | 50 | 6.6 |
| G (Control) (Fresh, unfixed Bovine Coronary Artery) | | | | 13.0 |

The modulus of elasticity of each of the six (6) treated samples and the one (1) untreated (control) sample are shown in TABLE 1. The modulus of elasticity of a biomaterial reflects its strain change as a result of applied stress. The lower the modulus of elasticity, the softer and more pliable the material.

As shown in TABLE 1, the modulus of elasticity of the treated samples (A through F) varied inversely with the percentage of longitudinal retraction applied, with the highest modulus of elasticity being observed in the sample treated under the least longitudinal retraction (0%) and the lowest modulus of elasticity being observed in the sample treated under the greatest longitudinal retraction (50%).

Given the fact that the measured modulus of elasticity of the untreated control sample (Sample G) was 13.0 psi, these data indicate that a modulus of elasticity equivalent to that of fresh unfixed coronary artery will be observed in segments of artery fixed under a longitudinal compression of between 40% to 50% and, thus, in this example it would be preferable to employ a longitudinal compression of 40% to 50%.

Current laboratory data indicates that, although static longitudinal compression has the effect of improving pliability of the cross-linked graft, no such improvement in graft pliability is observed when static longitudinal extension or stretching is applied.

B. A Second Embodiment: Dynamic Manipulation of the Collagenous Graft Material During Fixation The second preferred embodiment of the present invention comprises repeatedly manipulating or moving (e.g. stretching, contracting, twisting, flexing) the collagenous graft material to cause dynamic movement or flexing of collagen fibers within the graft, relative to one another, while at least a portion of the collagen cross-linking reaction is occurring. Such repetitive movement of the graft material causes changes in the positional and spacial relations of the collagen molecules and/or collagen fibers within the graft, relative to one another, while the intra-and/or intermolecular cross-linkages are being formed. As a result, the intra-and/or intermolecular cross-linkages are formed at different locations on the collagen molecules and/or collagen fibers than if the cross-linking reaction were to have been carried out while the graft remained in a relaxed, unstressed state.

This repetitive manipulation of the collagenous graft has its greatest effect on resultant pliability of the graft when carried out during the initial period of exposure to the collagen cross-linking fixative agent. This heightened effectiveness during the initial stage of the collagen cross-linking reaction is likely due to the fact that the individual collagen fibers are only free to move or change position relative to one another before a substantial number of inter- or intramolecular cross-linkages have been formed. If, however, a substantial number of inter- or intramolecular cross-linkages are formed before said dynamic manipulation is begun, the presence of such cross-linkages may prevent the collagen fibers from freely moving relative to one another, thereby preventing the dynamic manipulation from altering the locations and/or orientations of collagen cross-linkages from those which would be formed if the graft were fixed without any such manipulation or movement thereof. The actual time period during which the stretching-relaxation process is most effectively applied varies depending on the kinetics of the cross-linking reaction. For example, when a fast acting cross-linking reagent such as glutaraldehyde is used, the collagen modulating effect is most effective during approximately the initial sixty (60) seconds of the fixation process. When a slow acting cross-linking reagent such as a polyepoxy compound is used, the collagen modulating effect is most effective during the first 0.1 to 10.0 hours of the fixation process, and preferably during the first two (2) hours thereof.

i. Dynamic Longitudinal Stretching

One means of dynamically manipulating or moving the collagenous graft material during fixation is to subject the collagenous graft material to repetitive longitudinal stretching during at least a portion of the chemical cross-linking process.

In accordance with this aspect of the invention, the graft material may be fixed on the outer surface of a tube, rod, mandrel, plate, jig or other support member. It is preferable that the support member have a smooth outer surface upon which the graft material may slide, thereby allowing the graft material to be intermittently (a) stretched and (b) relaxed while remaining disposed on the surface of the support member.

One or more sides or ends of the graft material is/are attached to the support member by way of an attachment member such as a ligature or clip. The opposing sides and/or ends opposite the previously attached sides and/or ends of the graft material are then grasped by a movable clamp member(s) or other gripping apparatus. The graft material is then immersed in fixative solution and the movable clamp member(s) is/are moved away from the opposite sides and/or ends of the graft so as to stretch the graft material by a predetermined amount. The amount of stretching (e.g. the distance of travel of the movable clamp member in a direction away from the opposite end of the graft) is controlled and limited so as not to tear the graft and, preferably, so as not to exceed the degree of stretching which the graft is capable of withstanding without damage to or weakening of the graft.

In cases where the graft consists of a segment of artery, the artery segment is preferably stretched along its longitudinal axis to a length which is 5% to 60% and preferably about 5% to 30% longer than its original unstretched length.

Figure 2A:
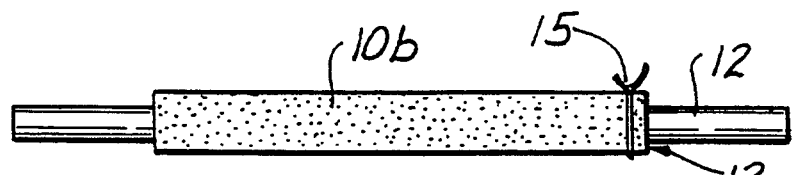
Figure 2B:
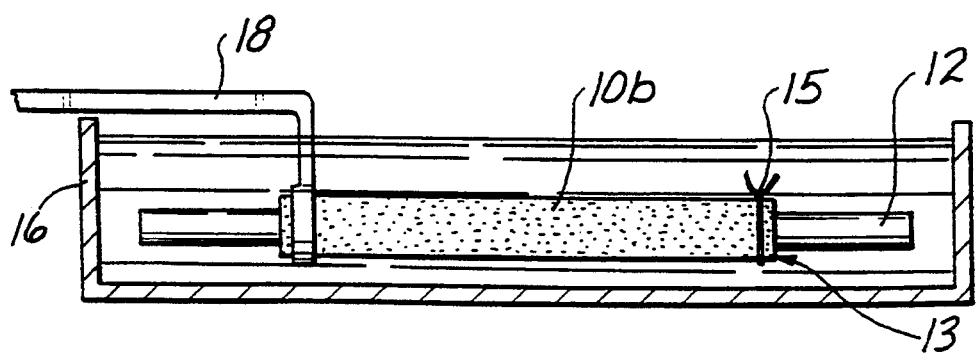

The graft is held in its stretched state (FIG. 2c) for a predetermined period of time and, thereafter, the stretching force is removed, thereby allowing the movable clamp member to move back toward the opposite end of the graft to a point where the graft has returned to a relaxed, unstretched state.

The above-described cycle of stretching-relaxation of the collagenous graft material is carried out repeatedly during at least the initial phase or initial time period of the chemical cross-linking reaction.

EXAMPLE 2

Preparation of a Pliable Coronary Artery Bypass Graft Under Dynamic Longitudinal Stretching This example is illustrated in FIGS. 2a-2e.

A segment of bovine coronary artery 10b is harvested, cleaned and ligated in the manner described in Example 1. After such harvesting, cleaning and ligating has been completed, the segment of artery 10b is slidably advanced onto the outer surface of a cylindrical support member 12 or rod. The outer diameter of support member 12 is equal to or slightly larger than the internal diameter of the segment of artery 10b.

After the segment of artery 10b has been disposed upon the support member 12, a first end 13 of the artery is firmly fixed to the support member 12 by a ligature 15. A movable clamp member 18 is attached to the opposite end of the artery. The artery is then immersed in a chemical bath 16 containing the 2% (vol.) Denacol ™ Ex-313 solution described in Example 1. As in Example 1, the solution within the bath is maintained at room temperature.

Immediately after the segment of artery 10b has been immersed in the solution within the bath 16, the end of the artery to which the movable clamp member 18 is attached is pulled away from the opposite end of the artery (arrow A) so as to longitudinally stretch the artery to a length which is 20% longer than its original unstretched length (FIG. 2c).

The amount of stretching necessary to achieve the desired pliability of the fixed graft will vary depending on the types of graft tissue being employed and the particular fixant being used. Typically, for arterial segments, the length of the segment will be increased by 5% to 60% of its original unstretched length. Care should be taken to ensure that the stretching of the graft does not exceed the elastic capabilities of the graft, as such may cause possible perforation, tearing or weakness of the graft. It is desirable that the amount of stretching applied be within the range of that which the graft would encounter during normal physiological functioning.

In this example, the segment of artery 10b is maintained in the stretched configuration (FIG. 2c) for approximately 2 to 5 seconds. Thereafter, the movable clamp member 18 is released and moved in the direction of Arrow B to a point where the segment of artery 10b has returned to an unstretched, relaxed state. This stretch/release cycle is repeated once every 1 to 5 minutes during the initial 0.1 hour to 2 hours of exposure to the 2% Denacol ™ Ex-313 fixative (i.e. 30 stretch-relax cycles are carried out during the first hour of exposure to the 2% Denacol ™ Ex-313 fixative).

In this example, during the initial 2 hours of fixation, the Denacol ™ Ex-313 solution was replaced 4 times (i.e. once every 30 minutes) to ensure optimal reactivity of the solution.

The preferred overall fixation period for this 2% Denacol ™ Ex-313 fixative is at least 48 hours. Thus, after the repetitive stretch-relax process has been completed during the initial 2 hours of exposure to the fixative, the artery 10a was subsequently allowed to remain immersed in the chemical fixative, the movable clamp member 18 may be removed from the free end of the segment of artery 10b and a lid 18 may be placed on the bath 16 as shown in FIG. 2d, so as to form a pressure tight seal therein. A fluid pressure source P is then applied to the solution within the bath 16 so as to maintain the solution under a pressure of approximately 30 mm·Hg. After the entire forty-eight (48) hours fixation time period has elapsed, the pressure source P is removed from the fixative bath 16, the lid 18 is removed, the ligature 15 is untied and the segment of artery 10b is slidably extracted and removed from the cylindrical support member 12.

Thereafter, the segment of artery is washed and stored in a suitable liquid such as ethanol.

ii. Dynamic Radial Stretching

With respect to luminal or tubular graft materials, another means of dynamically, manipulating or moving the collagenous graft material during fixation is to subject the collagenous graft material to repetitive radial stretching during the chemical cross-linking process.

Figure 3B:
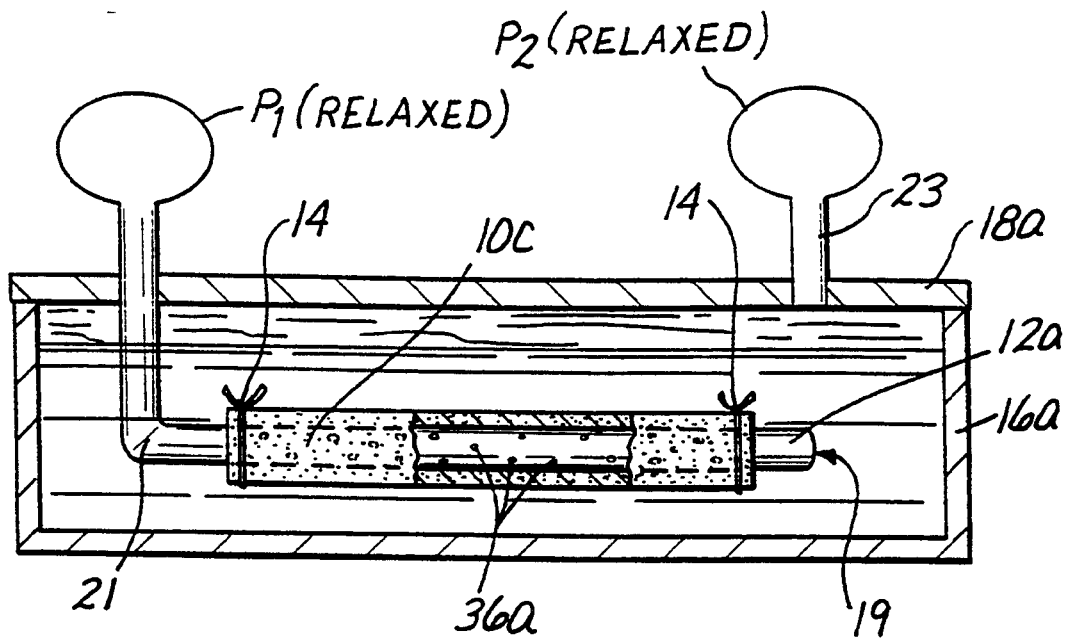

In accordance with this aspect of the invention, as illustrated in FIGS. 3a–3b, the graft material may be fixed on the outer surface of a hollow tube, rod, mandrel plate, jig or other support member and the ends of the graft material are firmly affixed thereto by way of ligatures, clips, tie wraps or other fixture means. Thereafter, the graft material is immersed or otherwise exposed to a fixant solution and pressurized fluid is passed into the lumen of the tubular or annular graft, between the ligatures, ties, clamps or other fixture members, thereby causing the graft to radially dilate or stretch. Thereafter, the fluid pressure within the graft is decreased, allowing the graft to return to a relaxed unstretched state.

The amount of radial stretching of the graft is controlled and limited so as not to tear the graft and, preferably, so as not to exceed the degree of radial stretching which the graft is capable of withstanding without damage to or weakening of the graft.

In cases where the graft consists of a segment of artery, the artery segment is preferably radially stretched to a radius which is 1% to 15% larger than the original unstretched radius of the segment of artery.

The graft material is held in the radially stretched state for 3 to 5 seconds and immediately thereafter the pressure within the graft is rendered equal to the pressure surrounding the graft so as to return the graft to its relaxed, unstretched state. The graft is allowed to remain in such relaxed, unstretched state for 2 to 30 minutes and preferably 5 to 10 minutes. Thereafter, this cycle of radial stretching-relaxation, as described herein, is repeated.

The above-described cycle of radial stretching-relaxation is carried out repeatedly during at least the initial portion of the collagen cross-linking reaction. In instances where slow reacting cross-linking agents (e.g. polyepoxy compounds) are used it is typically desirable to carry out the dynamic radial stretching-relaxation process throughout the first 1 to 2 hours of exposure to the fixative agent. Thereafter, the dynamic radial stretching-relaxation process is terminated and the graft may be allowed to remain immersed in the slow acting fixant solution at atmospheric or greater than atmospheric pressures for an additional period of 24 or more hours until the collagen cross-linking reaction has reached its desired point of completion.

The following Example No. 3 illustrates one application of dynamic radial stretching as a means for preparing pliable coronary artery bypass grafts of biological origin.

EXAMPLE 3

Preparation of a Pliable Coronary Artery Bypass Graft Via Dynamic Radial Stretching.

This example is illustrated in FIGS. 3a–3b.

A segment of bovine coronary artery 10c is harvested, cleaned and ligated as described in Example 1.

After the harvesting, cleaning and ligation of the segment of artery 10c has been completed, the segment of artery 10c is slidably advanced onto the outer surface of a hollow cylindrical support member 12a. The hollow cylindrical support member 12a has a closed distal end 19 and a hollow inner boar extending therethrough. A plurality of fluid outflow apertures 36a are formed in the mid-region of the cylindrical support member 12a so as to reside adjacent the luminal surface of the artery 10c when disposed on the cylindrical support member 12a.

After the segment of artery 10c has been slidably advanced on to the outer surface of the cylindrical support member 12a such that the fluid outflow apertures 36a reside adjacent the luminal surface of the artery 10c, ligatures 14 are tied about either end of the artery to securely fix the end of the artery to the cylindrical support member 12a. It is preferable that the ligatures 14 be tied sufficiently tight so as to withstand a build up of positive pressure within the segment of artery 10c which is up to approximately 5 psi greater than the pressure outside of the artery 10c.

A first liquid supply tube 21 is in fluid communication with the inner boar of the cylindrical support member 12a and is attached to a container of the 2% Denacol TM Ex-313 fixative solution having a variable pressure apparatus for varying the pressure $P_1$ of fixative solution flowing into the inner bore of the cylindrical support member 12a through the liquid supply tube 21 and ultimately within the lumen of the artery 10c. Any resident air or gas is purged from the liquid supply tube 21 and the inner bore of the cylindrical support member 12a such that the liquid supply tube 21 and the entire inner boar of the cylindrical support member 12a are filled with the fixative liquid and free of air bubbles.

With the segment of artery 10c disposed on the cylindrical support member 12a, the support member 12a and artery 10c are immersed in a bath 16a filled with the 2% Denacol TM Ex-313 fixative solution. A lid 18a is placed over the bath 16a to form a liquid tight seal thereon. A second fluid supply tube 23 passes into the closed inner chamber of the bath 16a and is attached to a second container of the 2% Denacol TM Ex-313 fixative solution. This second container of fixative solution is also provided with a variable pressure apparatus for varying the pressure $P_2$ of fixant liquid passing through the second fluid supply tube 23 and into the bath 16a.

Immediately after the artery 10c has become immersed in the bath 16a and the lid 18a has been firmly mounted in place, the pressure $P_1$ on the first fixative container and the pressure $P_2$ on the second fixative container are adjusted, relative to one another, such that the pressure of fixative liquid in the bath 16a surrounding the artery 10c is approximately 0.1 to 5.0 psi less and preferably 0.1 to 2.5 psi less than the pressure of fixative liquid within the lumen of the artery 10c. As a result, the pressure of fixative liquid within the artery 10c, relative to the pressure surrounding the artery 10c, will cause the artery 10c to radially stretch or dilate as shown in FIG. 3a.

Referring to FIG. 3a, in this example, $P_1$ (stretched) is about 3.0 psi while $P_2$ (stretched) is about 0.5 psi. The resultant pressure differential of 2.5 psi causes the artery 10c to stretch to a stretched radius that is approximately 8% greater than its relaxed unstretched radius. The artery 10c is held in such radially stretched state for 3 to 5 seconds and, thereafter, the pressures $P_1$ (relaxed) and $P_2$ (relaxed) are made equal to one another such that the segment of artery 10c will return to a relaxed unstretched state as shown in FIG. 3b.

The above-described radial stretching-relaxation cycle is repeated 30 times during the first hour of exposure to the fixant solution (about once every two minutes during the first hour). Thereafter, the pressure $P_1$ on the luminal surface of the artery 10c is made to equal atmospheric pressure and the pressure $P_2$ on the bath solution surrounding the artery 10c is made to equal approximately 3 psi. Such 3 psi pressure $P_2$ is maintained for the 47-hour period following the first hour of fixation during which the radial stretching-relaxation cycle was carried out. At the end of the 48-hour total exposure to the fixant solution within bath 16a, the pressure $P_2$ is made equal to atmospheric, the lid 18a is removed, ligatures 14 are removed and the segment of artery 10c is slidably extracted from the outer surface of the cylindrical support member 12a.

Thereafter, the segment of artery 10c is washed and stored in a suitable liquid (e.g. ethanol).

iii. Dynamic Radial Contraction

With respect to luminal or tubular graft materials, (e.g. segments of blood vessel) another means of dynamically moving or manipulating the collagen fibers within the graft during chemical fixation is to subject the collagenous graft material to repetitive radial contraction during the chemical cross-linking process.

In accordance with this aspect of the invention, the graft material is disposed on the outer surface of a hollow tube, rod, mandrel, plate, jig or other generally cylindrical support member having ends which are at least equal in diameter to the inner luminal diameter of the unstretched, relaxed graft and a mid-region (between the two ends) which has a diameter less than the inner luminal diameter of the unstretched, relaxed graft, and the ends of the graft material are firmly affixed thereto by way of ligatures, clips, tie wraps or other fixture means. Thereafter, the graft material is immersed or otherwise exposed to a fixant solution. After immersion in the fixant solution a pressurized fluid (e.g. more fixant solution) is passed onto the exterior wall of the tubular or annular graft, between the ligatures, ties, clamps or other fixture members, thereby causing the graft to radially contract against the mandrel or rod. Thereafter, the fluid pressure within the graft is decreased, allowing the graft to return to a relaxed unstretched state.

The amount of radial contraction of the graft is controlled and limited so as not to tear the graft and so as not to exceed the degree of radial contraction which the graft is capable of withstanding without damage to or weakening of the graft.

In cases where the graft consists of a segment of artery, the artery segment is preferably radially contracted to a radius which is 2% to 15% smaller, and preferably 2% to 10% smaller than the original uncontracted radius of the segment of artery.

The graft material is held in the radially contracted state for 2 to 5 seconds. Immediately thereafter, the pressure within the graft is rendered equal the pressure surrounding the graft so as to return the graft to a relaxed, uncontracted state and is allowed to remain in said uncontracted state for a second time period, of about 2 to 30 minutes and preferably about every 2 to 10 minutes.

The above-described cycle of radial contraction-relaxation is carried out repeatedly during at least the initial portion of the collagen cross-linking reaction. In instances where slow reacting cross-linking agents (e.g.

polyepoxy compounds) are used it is typically desirable to carry out the dynamic radial contraction-relaxation process throughout the first 1 to 2 hours of exposure to the fixative agent. Thereafter, the dynamic radial contraction-relaxation process is terminated and the graft may be allowed to remain immersed in the slow acting fixant solution at atmospheric or greater than atmospheric pressures for any additional period (e.g. 24 hours or more) until the collagen cross-linking reaction has reached its desired point of completion.

The following Example No. 4 illustrates one application of dynamic radial contraction as a means for preparing pliable coronary artery bypass grafts of biological origin.

EXAMPLE 4

Preparation of a Pliable Coronary Artery Bypass Under Dynamic Radial Contraction.

Figure 4:
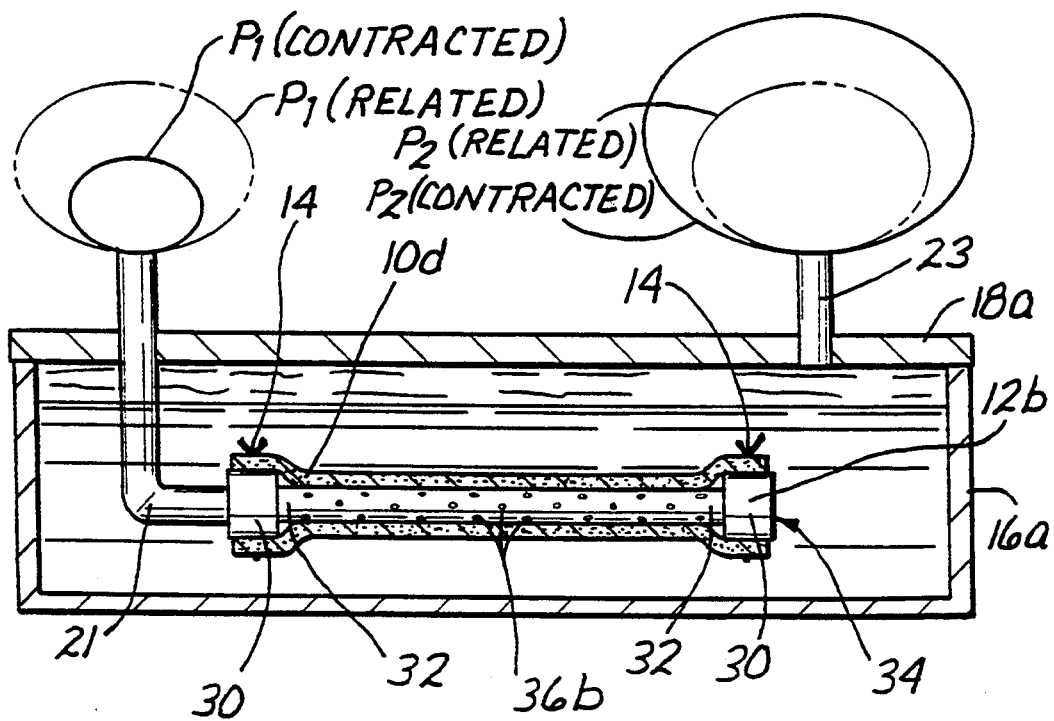
FIG. 4 is a diagram of a preferred method and apparatus for preparing pliable vascular grafts by dynamic radial contraction.
Figure 5A:
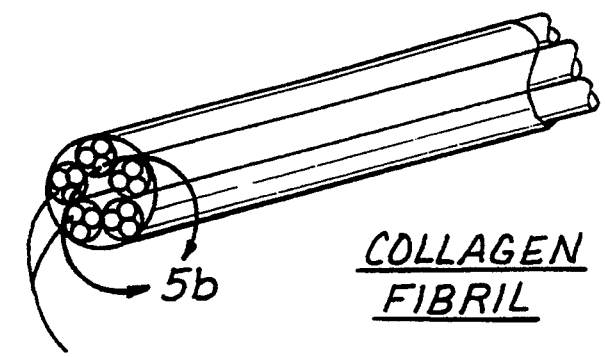
FIG. 5a is an illustration of a typical collagen fibril comprising five individual collagen molecules.
Figure 5B:
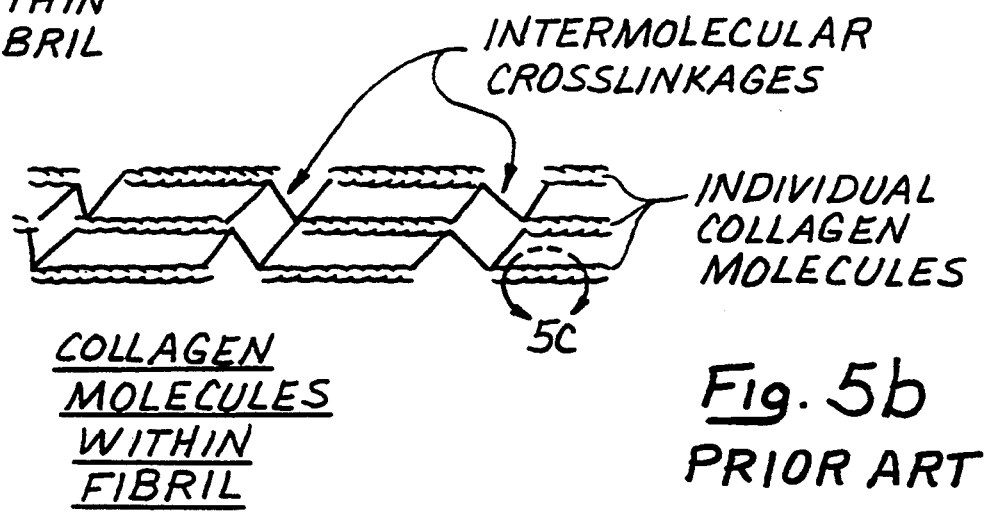
FIG. 5b is a schematic illustration of segment b—b' of FIG. 5a, showing the positioning of intermolecular cross-linkages between collagen molecules.
Figure 5C:
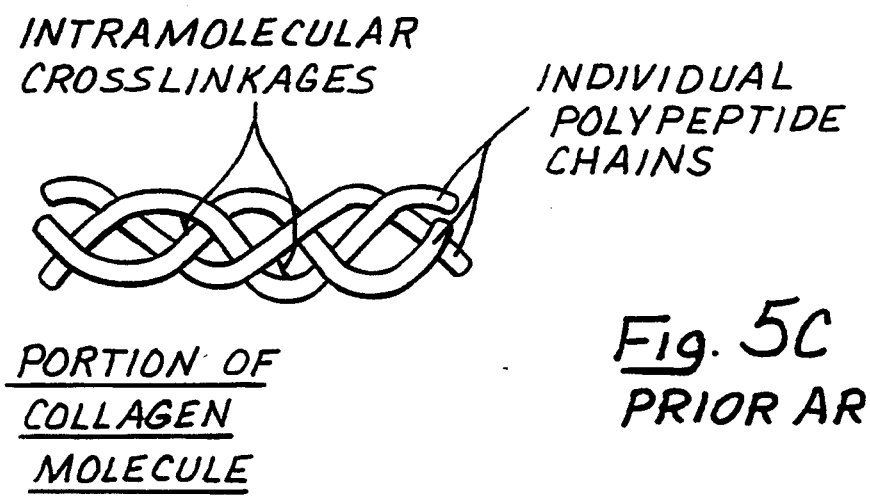
FIG. 5c is an enlarged schematic illustration of segment c—c' of FIG. 5b, showing the positioning of intramolecular cross-linkages between the polypeptide chains of the collagen molecule.

This example is illustrated in FIG. 4.

A segment of bovine coronary artery 10d is harvested, cleaned and ligated as described in Example 1.

After the harvesting, cleaning and ligation of the segment of artery 10d has been completed, the segment of artery 10d is slidably advanced onto the surface of a hollow, generally cylindrical support member 12b. The hollow, generally cylindrical support member 12b has an open or hollow inner bore extending therethrough and a fluid tight seal or cap formed on the distal end 34 thereof, thereby sealing and closing the hollow inner bore of the support member 12b at the distal end 34 thereof.

The first and second end portions 30 of the support member 12b are of a diameter equal to or slightly greater than the unstretched inner diameter of the segment of artery 10d. The mid-region 32 of the support member 12b has an outer diameter which is less than the inner luminal diameter of the relaxed unstretched segment of artery 10d. One or more fluid flow apertures 36b are formed in the mid-region 32 of the support member 12b so as to provide inflow and outflow of fluid from the inner bore of the support member 12b.

A first liquid supply tube 21 is in fluid communication with the inner bore of the reduced diameter support member 12b and is attached to a container of 2% Denacol ™ Ex-313 fixative solution having a variable pressure apparatus for varying the pressure $P_1$ of fixative solution flowing into the inner bore of the reduced diameter support member 12b through the first liquid supply tube 21. Any resident air or gas is purged from the liquid supply tube 21 and the inner bore of the reduced diameter support member 12b such that the first liquid supply tube 21 and the entire inner bore of the support member 12b are filled with fixative liquid and free of air bubbles.

With the segment of artery 10d disposed on the reduced diameter support member 12b, the support member 12b and artery 10d are immersed in a bath 16a filled with the 2% Denacol ™ Ex-313 fixative solution. A lid 18a is placed over the bath 16a to form a liquid tight seal thereon. A second fluid supply tube 23 passes into the closed inner chamber of the bath 16a and is attached to a second container of the 2% Denacol ™ Ex-313 fixative solution. This second container of fixative solution is also provided with a variable pressure apparatus for varying a pressure $P_2$ of fixant liquid passing through the second fluid supply tube 23 and into the bath 16a.

Immediately after the artery 10d has become immersed in the bath 16a, the lid 18a is firmly mounted in place, the pressure $P_1$ on the first fixative container and the pressure $P_2$ on the second fixative container are adjusted relative to one another such that the pressure of fixative liquid in the bath 16a surrounding the artery 10d is 0.125 to 5.0 psi greater, and preferably 0.1 to 2.5 psi greater, than the pressure of the fixative liquid within the lumen of the artery 10d. As a result, the pressure of fixative liquid within the artery 10d, relative to the pressure surrounding the artery 10d, will cause the artery 10d to radially contract or draw inwardly about the reduced diameter mid-region 32 of the reduced diameter support member 12b, as shown in FIG. 4.

Referring to FIG. 4, in this example, $P_1$ (contracted) is about 0.5 psi while $P_2$ (contracted) is about 3.0 psi. The resultant pressure differential of 2.5 psi causes the artery 10d to contract inwardly upon the reduced diameter mid-region 32 of the support member 12b. In this example, the reduced diameter mid-region 32 of the support member 12b is 8% smaller in diameter than the relaxed unstretched diameter of the artery 10d, thus this 2.5 psi pressure differential will result in an 8% decrease in the diameter of the artery 10d. The artery 10d is held is such radially contracted state for 3 to 5 seconds and, thereafter, the pressures $P_1$ (relaxed) and $P_2$ (relaxed) are made equal to one another such that the segment of artery 10d will return to a relaxed, uncontracted state. The segment of artery was then allowed to remain in such relaxed, uncontracted state for a period of about 2 minutes.

The above-described radial contraction-relaxation cycle is repeated about 30 times during the first hour of exposure to the fixant solution (about once every 2 minutes during the first hour). Thereafter, the pressure $P_1$ on a luminal surface of the artery 10d and the pressure $P_2$ within the bath 16a are made equal such that the artery 10d will assume an uncontracted, unstretched state. The artery is then permitted to remain in such uncontracted, unstretched state, with fixant solution inside and outside the artery for an additional 47-hour period following the first hour of fixation during which the radial contraction-relaxation cycle was carried out. At the end of the 48-hour total exposure to the fixant solution within bath 16a, the pressure $P_2$ is made equal to atmospheric, the lid 18a is removed, ligatures 14 are removed and the segment of artery 10d is slidably extracted from the outer surface of the reduced diameter support member 12b.

Thereafter, the segment of artery 10d is washed and stored in a suitable liquid (e.g. ethanol).

It will be understood that the invention has been described herein with specific reference to certain preferred embodiments and certain specific examples. It will be appreciated that those skilled in the art may make numerous additions, modifications, alterations and variations to such preferred embodiments and examples without departing from the spirit and scope of the invention. For example, although the invention has been described herein with particular reference to arterial vascular grafts, it will be appreciated that the methods of the present invention may be applied to virtually any collagenous biological tissue including, but not limited to, skin grafts, heart valve annulae, heart valve leaflets, conduit grafts and ureter grafts. It will be further appreciated that specially shaped jigs, fixtures or support members may be devised for holding such tissues during compression and/or stretching thereof in accordance with the present invention. Also, with respect to specific examples disclosed, it will be appreciated that the time course of the treatment and/or exposure times to the fixative reagents may be varied without departing from the methodology of the present invention. For example, it may be desirable to dynamically stretch, compress or contract a segment of blood vessel approximately 72 times a minute so as to mimic the normal heart rate and normal pulsatile movement that would be encountered by the blood vessel in situ.

Accordingly, it is intended that all foreseeable additions, modifications, alterations and variations, including but not limited to those specifically mentioned herein, not be included within the scope of the following claims.

What is claimed is:

1. A method of preparing a flexible collagenous biological graft material comprising a network of collagen fibers, said method comprising the step of:
   (a) longitudinally compressing the network of collagen fibers while exposing the collagen fibers to a collagen cross-linking reagent.

2. The method of claim 1 further comprising the steps of:
   i. placing the graft material on a smooth surfaced support member;
   ii. exerting a compressive force on said graft material to place said graft material in a longitudinally compressed state;
   iii. maintaining the graft material in said compressed state;
   iv. immersing the compressed graft material in the collagen cross-linking reagent for a period of time sufficient to effect adequate fixation of the collagen fibers within the graft material;
   v. removing the graft material from the collagen cross-linking reagent; and
   vi. removing the graft material from said compressed state and from the support member.

3. The method of claim 2 wherein step (ii.) further comprises:
   compressing said graft material along its longitudinal axis to a compressed state so that the graft material is decreased in length by an amount equal to about 1% to 50% of its original length.

4. The method of claim 2 wherein step (ii.) further comprises:
   compressing said graft material along its longitudinal axis to a compressed state so that the graft material is decreased in length by an amount equal to about 5% to 30% of its original length.

5. The method of claim 2 wherein step (iv.) comprises immersing the graft material in a liquid solution of polyepoxy fixative for at least 24 hours.

6. The method of claim 5 wherein "immersing the graft material in a liquid solution of polyepoxy fixative" comprises:
   immersing the graft material in a 2% (vol.) aqueous solution of glycerol triglycidyl ether.

7. A collagenous biological vascular graft prepared by a method which comprises the steps of:
   (a) harvesting a segment of blood vessel having a luminal surface and a network of collagen fibers from a mammalian source;
   (b) placing the segment of blood vessel on a cylindrical support member having an outer surface such that the luminal surface of the blood vessel is in contact with the outer surface of the cylindrical support member;
   (c) longitudinally compressing the segment of blood vessel to a compressed length so that the segment of blood vessel is shortened by an amount equal to 1% to 50% of its original relaxed length;
   (d) immersing the longitudinally compressed segment of blood vessel in a collagen cross-linking reagent for a period of time sufficient to achieve adequate cross-linking of the collagen fibers contained in the segment of blood vessel;
   (e) removing the segment of blood vessel from the collagen cross-linking reagent;
   (f) releasing the segment of blood vessel from said longitudinally compressed state and removing the segment of blood vessel from the outer surface of said cylindrical support member.

8. The biological vascular graft of claim 7 wherein step (c) comprises:
   longitudinally compressing the segment of blood vessel to a compressed length so that the segment of blood vessel is shortened by an amount equal to 40% to 50% of its original relaxed length.

* * * * *